US009144410B1

(12) United States Patent  
Chen et al.

(10) Patent No.: US 9,144,410 B1  
(45) Date of Patent: Sep. 29, 2015

(54) APPARATUS AND METHOD FOR RETROFITTING AN INTRAORAL RADIOLOGY POSITIONING DEVICE WITH A RECTANGULAR COLLIMATION DEVICE

(71) Applicant: Cyber Medical Imaging, Inc., Los Angeles, CA (US)

(72) Inventors: Adam Chen, Pacific Palisades, CA (US); Douglas C Yoon, Beverly Hills, CA (US)

(73) Assignee: Cyber Medical, Inc., Los Angeles, CA (US)

( * ) Notice: Subject to any disclaimer, the term of this patent is extended or adjusted under 35 U.S.C. 154(b) by 59 days.

(21) Appl. No.: 13/920,472

(22) Filed: Jun. 18, 2013

Related U.S. Application Data

(60) Provisional application No. 61/661,322, filed on Jun. 18, 2012.

(51) Int. Cl.  
    *G01K 1/02*     (2006.01)  
    *A61B 6/14*     (2006.01)  
    *G21K 1/02*     (2006.01)

(52) U.S. Cl.  
    CPC ............... *A61B 6/145* (2013.01); *G21K 1/025* (2013.01)

(58) Field of Classification Search  
    CPC ............. A61B 6/145; A61B 2019/204; G03B 42/042; G03B 42/025  
    USPC .................................. 378/170, 168, 174, 191  
    See application file for complete search history.

(56) References Cited

U.S. PATENT DOCUMENTS 4,554,676 A * 11/1985 Maldonado et al. .......... 378/170  
6,343,875 B1     2/2002 Eppinger et al.

* cited by examiner

*Primary Examiner* — Hoon Song  
(74) *Attorney, Agent, or Firm* — Roy L Anderson; Wagner, Anderson & Bright

(57) ABSTRACT

A variable aperture X-ray collimating device that fits over existing intraoral radiographic sensor positioners enables clinicians to provide radiation protection for their patients while allowing the flexibility to accommodate various commercially available positioning kits. In addition, the variable aperture allows for easy accommodation of various sensor sizes.

15 Claims, 3 Drawing Sheets

APPARATUS AND METHOD FOR RETROFITTING AN INTRAORAL RADIOLOGY POSITIONING DEVICE WITH A RECTANGULAR COLLIMATION DEVICE

CROSS-REFERENCE TO RELATED APPLICATIONS

This application claims priority from U.S. Ser. No. 61/661,322, filed Jun. 18, 2012, the disclosure of which is specifically incorporated herein by reference.

FIELD OF THE INVENTION

The field of the present invention is dentistry and, specifically, devices used by dentists when taking intra-oral radiographs with dental X-ray film or an intra-oral digital dental sensor.

BACKGROUND OF THE INVENTION

The rectangular collimator is a dental device that has been used in conjunction with external positioning devices intended to give proper geometric alignment between the X-ray generator, the patient's teeth and the X-ray film or digital radiographic sensor. The purpose of the rectangular collimator is to restrict the size of the X-ray beam to approximately the size of the imaging field of the film or sensor. This protects the patient against unnecessary radiation exposure and improves image quality by reducing side scatter.

Such devices also improve image quality by reducing X-ray side scatter from anatomic structures outside the imaging field of view but within the uncollimated X-ray beam.

The main deficiency in the current design of all rectangular collimating devices is the user's inability to adjust the size of the rectangular opening to match that of the actual X-ray film or digital sensor size to minimize the non-imaging patient X-ray exposure.

There are three common sizes of intra oral x-ray film or digital sensors commonly used in dentistry: Size 0, size 1, and size 2. The existing rectangular collimators are usually slightly larger than the size 2 X-ray film or digital sensor.

A rectangular collimating device with the adjustability for the three different size imaging fields would further reduce the patient's X-radiation exposure by matching the rectangular opening of the collimator to the specific film or sensor size used.

SUMMARY OF THE INVENTION

The present invention is generally directed to attachments useful with an external ring and rod x-ray film or digital sensor holder system. An adjustable aperture rectangular collimating device will reduce the area of the active X-ray beam to properly match the active area of the X-ray film or digital sensor. This will promote better radiation hygiene in the dental profession and reduce unnecessary and unproductive X-ray exposure to the patient during dental X-ray exams.

Accordingly, it is primary object of the present invention to provide for an adjustable aperture rectangular collimating device to be used in conjunction with existing x-ray film or digital sensor holder systems.

This and further objects and advantages will be apparent to those skilled in the art in connection with the drawings and the detailed description of the invention set forth below.

DETAILED DESCRIPTION OF THE INVENTION

The present invention provides a retrofit solution for allowing an intraoral radiology positioning device to be retrofit with a rectangular collimation attachment.

Figure 1:
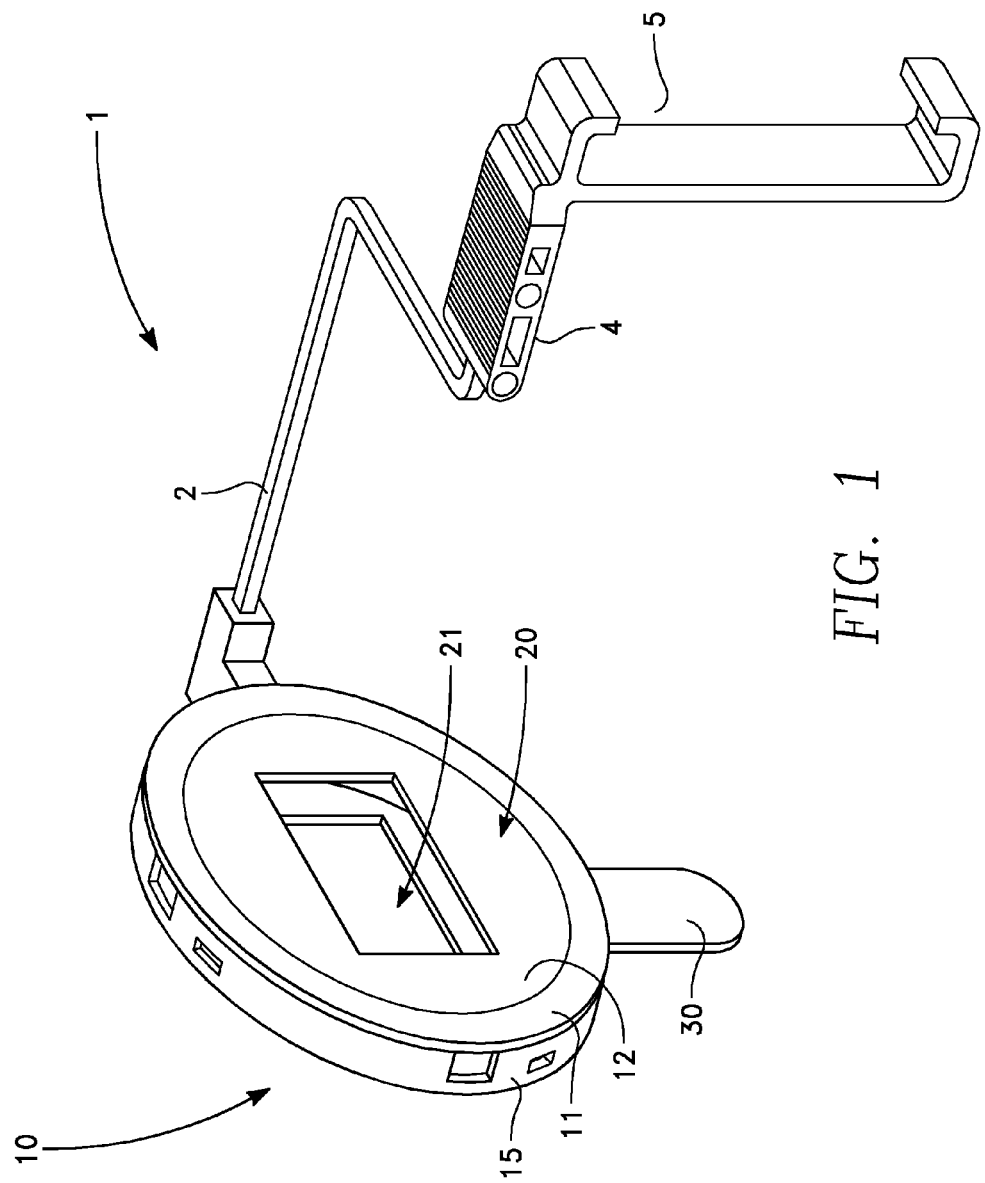
FIG. 1 illustrates a prior art intraoral radiology positioning device that has been retrofitted with a rectangular collimation attachment and FIG. 2 is an exploded view of FIG. 1 illustrating the near and far side cover of the rectangular collimation attachment of FIG. 1 detached from the intraoral radiology positioning device.
Figure 2:
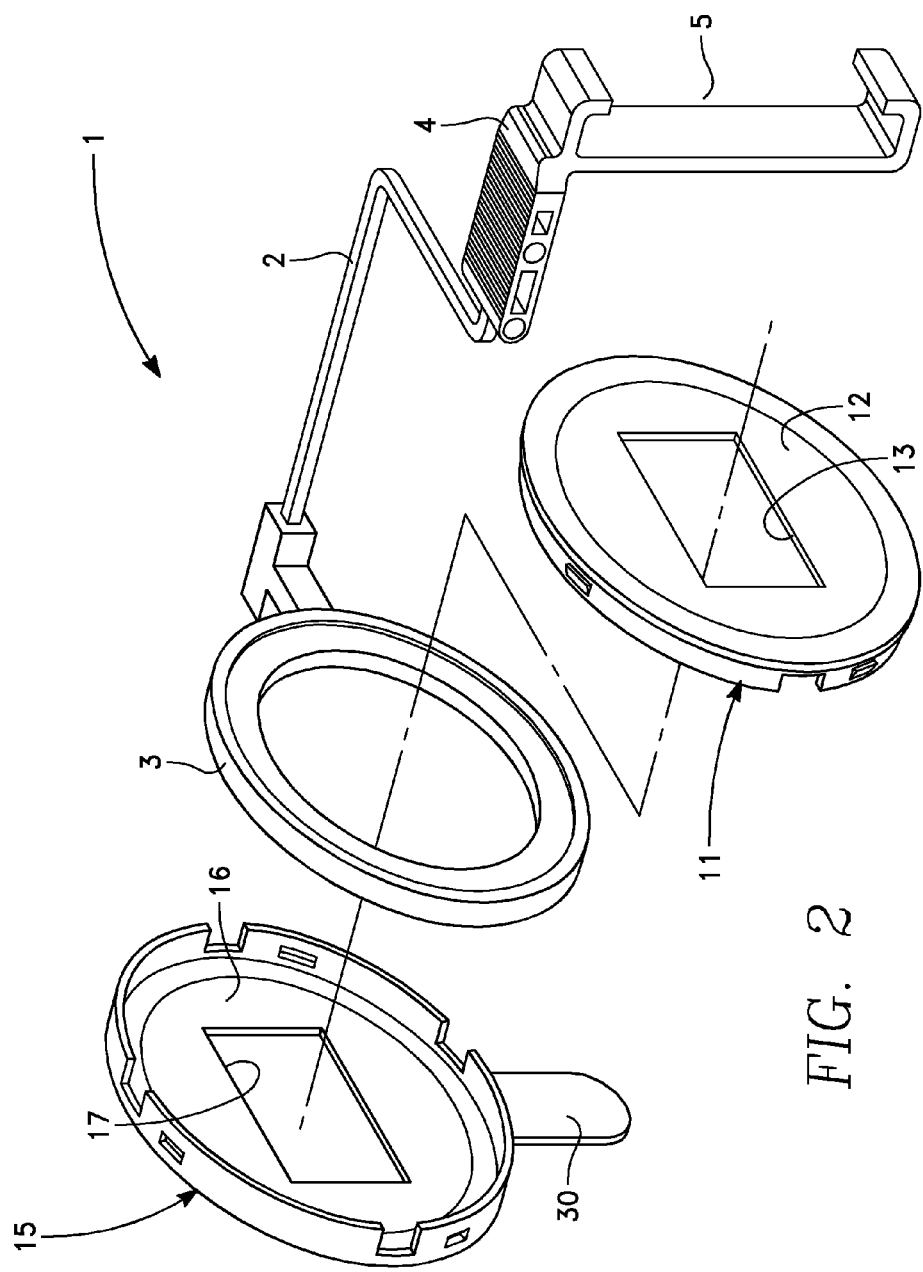

As illustrated in FIGS. 1 and 2, a standard intraoral radiology positioning device, generally designated as 1, has an a guide arm 2, an aiming ring 3 attached to guide arm 2, and bite block 4 and sensor basket 5 attached at one end of guide arm 2. Details of such a standard intraoral radiology positioning device are set forth in U.S. Pat. No. 6,343,875, the disclosure of which is specifically incorporated herein by reference.

The present invention provides a retrofit collimation attachment, generally designated as 10, which is designed to secure itself about guide arm 2 of intraoral radiology positioning device 1. Retrofit collimation attachment 10 is comprised of a near side cover 11 and a far side cover 15 (preferably made out of plastic that will withstand autoclaving) that are designed to fit about guide arm 2 and then releasably attach themselves together so as to secure a collimation plate, generally designated as 20, with a collimation aperture 21 that is within the opening of aiming ring 3 relative to an intraoral X-ray device. Either or both of near and far side covers 11 and 15 can be adapted to hold a collimation plate which will form collimation plate 20 and either or both of near and far side covers 11 and 15 can be fitted with one or more handles 30 for ease of use by a patient. It is especially preferred that near side cover 11 has its own near side collimation plate 12 having an aperture 13 and far side cover 15 has its own far side collimation plate 16 having an aperture 17, which allows the thickness of each such plate to be half what would otherwise be required to provide a sufficient amount of thickness for collimation plate 20 to block X-ray radiation. In an especially preferred embodiment, near and far side collimation plates 12 and 16 are made of stainless steel and each have a thickness of approximately 1 mm so that, together, the two plates will provide 2 mm of steel protection for collimation plate 20 and apertures 12 and 13 will be aligned so as to form collimation aperture 21.

Figure 3A:
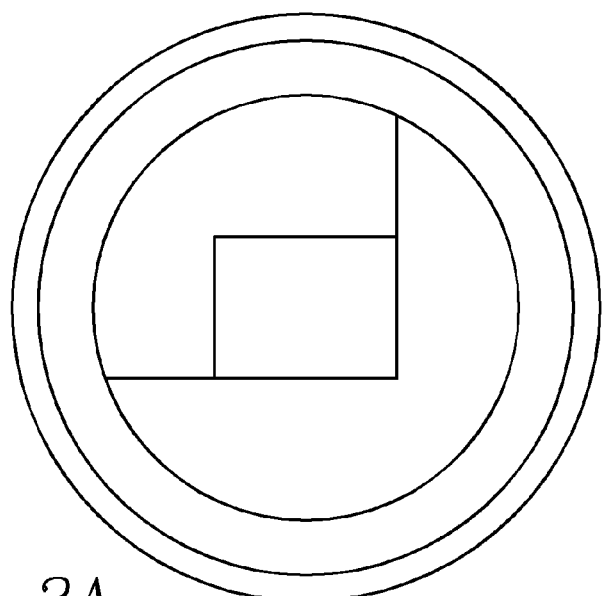
FIGS. 3A and 3B illustrate a retrofit rectangular collimation attachment according to the present invention with sliding shutters.
Figure 3B:
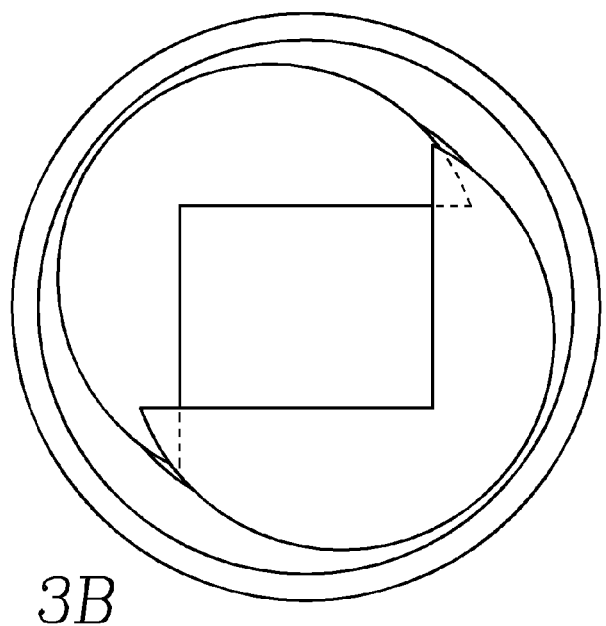

Because ease of use and adaptability are key goals of the present invention, it is especially preferred that retrofit collimation attachment 10 can easily be adapted to provide different sizes for collimation aperture 21 so that a user can choose the correct opening that corresponds to the proper size of the imaging media (size #1, #1, or #2), whether it be X-ray film or a digital sensor. A first way this can be accomplished is to simply use a different retrofit collimation attachment 10 for each different desired size of collimation aperture 21 (which will generally have a rectangular shape). A second way this can be accomplished is for one or both of near and far side collimation plates 12 and 16 to be readily detachable from, and thus easily interchangeable with, another plate with a different size aperture. Accordingly, either or both of near and far side collimation plates 12 and 16 might, for example, be snap fit into, respectively, near and far side covers 11 and 15. A third way this can be accomplished is for collimation aperture 21 to be adjustable (such as, by example, use of sliding shutters that can be moved between two or more positions as illustrated in FIG. 3).

Near and far side covers 11 and 15 should function together so as to provide a quick and easy way to releasably connect them together about aiming ring 3. An especially preferred way in which this can be accomplished is for near and far side covers 11 and 15 to snap-fit together, although any suitable means for such attachment can be used such as, but not limited to: threaded screw, ball and socket, friction grip, male/female connectors, clamp, magnetic, suction, fixed or removable adjustable ring/band, Velcro, single or double sided adhesive, inelastic ring/band, elastic ring/band, adjustable ring/band, and the like.

While the invention has been described herein with reference to certain preferred embodiments, those embodiments have been presented by way of example only, and not to limit the scope of the invention. Additional embodiments thereof will be obvious to those skilled in the art having the benefit of this detailed description.

Accordingly, it will be apparent to those skilled in the art that still further changes and modifications in the actual concepts described herein can readily be made without departing from the spirit and scope of the disclosed inventions.

What is claimed is:

1. An apparatus for retrofitting an intraoral radiology positioning device comprised of an aiming ring, a bite block and a sensor basket attached to a guide arm, comprising:
   a near side cover;
   a far side cover; and
   a first collimation plate with a first collimation aperture;
   wherein the near side cover and the far side cover are adapted so as to releasably attach together about the aiming ring so as to hold the first collimation plate and position the first collimation plate so that the first collimation aperture restricts the size of an X-ray beam traveling through the aiming ring;
   wherein the near side cover is adapted to be positioned adjacent to a near side surface of the aiming ring while the far side cover is adapted to be positioned adjacent to a far side surface of the aiming ring so that the aiming ring is positioned between the near side cover and the far side cover and neither the near side cover nor the far side cover is mechanically secured by itself to the aiming ring.

2. The apparatus of claim 1, wherein the first collimation plate is removable from the near and far side covers.

3. The apparatus of claim 2, further comprising a second collimation plate adapted to be held by the near and far side covers, said second collimation plate having a second collimation aperture of a different size than that of the first collimation aperture.

4. The apparatus of claim 1, wherein the first collimation plate is a single plate held by one of the near side cover and the far side cover.

5. The apparatus of claim 4, wherein the first collimation plate is releasably held by one of the near side cover and the far side cover.

6. The apparatus of claim 1, wherein the first collimation plate is adjustable between a first aperture size and a second aperture size.

7. The apparatus of claim 1, wherein the near side cover and the far side cover are held together by a snap fit.

8. An apparatus, comprising:
   an intraoral radiology positioning device comprised of an aiming ring, a bite block and a sensor basket attached to a guide arm;
   a near side cover;
   a far side cover; and
   a first collimation plate with a first collimation aperture;
   a second collimation plate with a first collimation aperture of a different size that that of the first collimation aperture;
   wherein the near side cover and the far side cover are adapted so as to releasably attach together about the aiming ring so as to hold the first collimation plate and the second collimation plate and position the first collimation plate and the second collimation plate so that the first collimation aperture and the second collimation aperture restrict the size of an X-ray beam traveling through the aiming ring;
   wherein the near side cover is adapted to be positioned adjacent to a near side surface of the aiming ring while the far side cover is adapted to be positioned adjacent to a far side surface of the aiming ring so that the aiming ring is positioned between the near side cover and the far side cover and neither the near side cover nor the far side cover is mechanically secured by itself to the aiming ring; and
   wherein at least one of the first and the second collimation plates is removable from the near and far side covers.

9. The apparatus of claim 8, wherein both the first collimation plate and the second collimation plate are removable from the near and far side covers.

10. A method for retrofitting an intraoral radiology positioning device comprised of an aiming ring, a bite block and a sensor basket attached to a guide arm, comprising the steps of:
    releasably attaching a near side cover and a far side cover together about the aiming ring so as to hold a collimation plate and position the collimation plate so that the collimation aperture restricts the size of an X-ray beam traveling through the aiming ring wherein the near side cover is positioned adjacent to a near side surface of the aiming ring while the far side cover is positioned adjacent to a far side surface of the aiming ring so that the aiming ring is positioned between the near side cover and the far side cover and neither the near side cover nor the far side cover is mechanically secured by itself to the aiming ring.

11. The method of claim 10, comprising the further step of adjusting the size of the collimation aperture between a first aperture size and a second aperture size.

12. The method of claim 11, wherein the size of the collimation aperture is adjusted by substituting a second collimation plate for the collimation plate.

13. An apparatus for retrofitting an intraoral radiology positioning device comprised of an aiming ring, a bite block and a sensor basket attached to a guide arm, comprising:
    a near side cover;
    a far side cover; and
    a collimation plate with a collimation aperture;
    wherein the near side cover and the far side cover are adapted so as to releasably attach together about the aiming ring so as to hold the collimation plate and position the collimation plate so that the collimation aperture restricts the size of an X-ray beam traveling through the aiming ring;

wherein the collimation plate is comprised of a near side collimation plate held by the near side cover and a far side collimation plate held by the far side collimation plate.

14. The apparatus of claim 13, wherein the near side collimation plate is releasably held by the near side cover and the far side collimation plate is releasably held by the far side cover.

15. The apparatus of claim 6, wherein the first collimation plate is adjustable between the first aperture size and the second aperture size by use of at least one sliding shutter that can be moved between two or more positions.

\* \* \* \* \*